(12) United States Patent
Staton et al.

(10) Patent No.: US 6,583,424 B2
(45) Date of Patent: Jun. 24, 2003

(54) SCANNING SYSTEM WITH CALIBRATED DETECTION AND METHOD

(75) Inventors: Kenneth L. Staton, San Carlos, CA (US); Andreas N. Dorsel, Menlo Park, CA (US)

(73) Assignee: Agilent Technologies Inc., Palo Alto, CA (US)

( * ) Notice: Subject to any disclaimer, the term of this patent is extended or adjusted under 35 U.S.C. 154(b) by 0 days.

(21) Appl. No.: 09/892,209

(22) Filed: Jun. 25, 2001

(65) Prior Publication Data

US 2002/0195554 A1 Dec. 26, 2002

(51) Int. Cl.[7] .............................................. G01N 21/64
(52) U.S. Cl. ................................ 250/461.2; 250/252.1; 250/459.1
(58) Field of Search ..................... 250/252.1, 459.1, 250/461.1, 461.2, 361 R

(56) References Cited

U.S. PATENT DOCUMENTS

| | | | |
|---|---|---|---|
| 3,891,853 A | | 6/1975 | Kremen et al. |
| 4,150,951 A | | 4/1979 | Capelle et al. |
| 4,295,199 A | * | 10/1981 | Curry et al. .................. 702/21 |
| 4,622,468 A | | 11/1986 | Stefanski et al. |
| 4,750,837 A | | 6/1988 | Gifford et al. |
| 4,802,768 A | | 2/1989 | Gifford et al. |
| 4,816,687 A | | 3/1989 | Fehrenbach et al. |
| 4,900,933 A | * | 2/1990 | Nestor et al. ............. 250/458.1 |
| 5,018,209 A | | 5/1991 | Bacus |
| 5,272,518 A | | 12/1993 | Vincent |
| 5,303,064 A | | 4/1994 | Johnson et al. |
| 5,325,171 A | * | 6/1994 | Shimizu ...................... 356/230 |
| 5,373,161 A | * | 12/1994 | Tararine et al. .......... 250/363.09 |
| 5,491,343 A | | 2/1996 | Brooker |
| 5,523,207 A | | 6/1996 | Kamentsky et al. |
| 5,548,115 A | * | 8/1996 | Ballard et al. ............... 250/253 |
| 5,600,147 A | | 2/1997 | Jensen |
| 5,635,402 A | | 6/1997 | Alfano et al. |
| 5,689,110 A | * | 11/1997 | Dietz et al. ............... 250/252.1 |
| 5,892,234 A | | 4/1999 | McKeever et al. |
| 5,981,958 A | | 11/1999 | Li et al. |
| 6,316,774 B1 | * | 11/2001 | Giebeler et al. .......... 250/458.1 |
| 6,329,661 B1 | * | 12/2001 | Perov et al. .............. 250/461.2 |
| 6,352,672 B1 | * | 3/2002 | Mabile et al. ........... 422/82.08 |
| 6,417,506 B1 | * | 7/2002 | Pinkel et al. ................ 250/216 |
| 6,471,916 B1 | * | 10/2002 | Noblett ..................... 422/82.08 |
| 6,496,309 B1 | * | 12/2002 | Bliton et al. ................ 359/618 |
| 2003/0012695 A1 | * | 1/2003 | Shalon et al. .............. 422/68.1 |

* cited by examiner

*Primary Examiner*—Constantine Hannaher
*Assistant Examiner*—Albert Gagliardi

(57) ABSTRACT

A self-calibrating scanning system and method are used in the analysis of biomolecules on a microarray. The self-calibrating scanning system comprises an excitation light source, an optical portion, a detection portion and a calibration portion that includes a calibration apparatus and compensation portion. The calibration apparatus comprises a light source having a highly reproducible or calibrated light based on a preselected or reference light level. The calibration apparatus emits the calibrated light that is measured by the detection portion of the scanning equipment. If the detection components are stable, the components will measure a constant output value for the calibrated light over time. As a detection component changes with time, the output value will change for the same calibrated light. The method comprises the steps of initially calibrating the detection portion of the scanning system and subsequently calibrating the detection portion to compensate for sensitivity changes.

29 Claims, 2 Drawing Sheets

_US 6,583,424 B2_

SCANNING SYSTEM WITH CALIBRATED DETECTION AND METHOD

TECHNICAL FIELD

This invention relates to calibration of detection systems for non-elastically scattered light. In particular, the invention relates to the calibration of scanners for detection of biomolecules on microarrays.

BACKGROUND ART

Microarrays of biomolecules, such as DNA, RNA, cDNA, polynucleotides, oligonucleotides, proteins, and the like, are state-of-the-art biological tools used in the investigation and evaluation of biological processes, including gene expression and mutation for analytical, diagnostic, and therapeutic purposes. Microarrays typically comprise a plurality of polymers, e.g., oligomers, synthesized or deposited on a substrate in an array pattern of features. The support-bound polymers are typically called "probes", which function to bind or hybridize with a sample of polymer material under test, i.e., a moiety in a mobile phase (typically fluid), called a "target" in hybridization experiments. However, some investigators also use the reverse definitions, referring to the surface-bound polymers as targets and the solution sample of polymer as probes. Further, some investigators bind the target sample under test to the microarray substrate and put the polymer probes in solution for hybridization. Either of the "target" or "probes" may be the one that is to be evaluated by the other (thus, either one could be an unknown mixture of polymers to be evaluated by binding with the other). All of these iterations are within the scope of this discussion herein. The plurality of probes and/or targets in each location in the array is known in the art as a "feature". A feature is defined as a locus onto which a large number of probes and/or targets all having the same monomer sequence are immobilized. In use, the array surface is contacted with one or more targets under conditions that promote specific, high-affinity binding of the target to one or more of the probes. The targets are typically labeled with an optically detectable label, such as a fluorescent tag, dye or fluorophore, so that the targets are detectable with scanning equipment after a hybridization assay. DNA array technology, for example, offers the potential of using a multitude (hundreds of thousands) of different oligonucleotides to analyze changing mRNA populations.

Typical scanning equipment used for biomolecular analysis, such as scanning fluorometers, comprise an excitation light source, an optical system for directing light to and from a sample being scanned, a detection system and optionally an analysis system. To analyze a microchip after a hybridization assay, the scanner scans a light from its excitation light source across the microchip. The light excites the optically detectable labels on the hybridized biomolecules. The excited labels in turn emit light at one or more particular wavelengths. The emitted light from the biomolecules is detected and measured by the detection system and the measurements are analyzed by analysis equipment to determine the results of the assay. In competitive hybridization assays, more than one label may be used, each of which emit light having a characteristic emission spectrum, which may be narrow or broad, to distinguish the biomolecules on the microchip. The light emitted by each different label must be separately detected by the scanning equipment for analysis. State-of-the-art scanners are equipped with a detection system having multiple channels for detecting emissions at different wavelengths, for example. The detection systems having multiple channels are designed to detect signals from a combination of dyes or dyes having broad emission spectra that are used in labeling. Parameters such as the intensity, the wavelength, and the location of the emitted light on the microchip provide important information about the target material being assayed. Therefore, accurate measurement of these parameters is essential to providing accurate information about the target material.

The detection systems used in scanning equipment comprise one or more detector components, such as photomultiplier tubes (PMTs). PMTs are known to age and to also deteriorate as a function of signals and overloads previously received.

An approach to improving the accuracy of a fluorometer used for scanning flow cells is to determine the relative fluorescence intensity or index (RFI) for a bulk sample in the flow cell. Gifford et al., U.S. Pat. Nos. 4,750,837 and 4,802,768, discuss and illustrate approaches for compensating for variations in excitation light using reference signals or reference paths, and the advantages and disadvantages of these approaches, and further, disclose a reference system that accounts for variations in signal levels from light sources and detection components that affect the RFI. A computation is made on measurements taken on the detection components and light sources, which indicates the relative concentration of the target being assayed using the flow cell. The computation is intended to cancel out the variations in the light sources and the detectors. The system described by Gifford et al. provides only a relative measurement of the target concentration in a bulk sample using flow cells. Therefore, there is little or no consistency between fluorometer systems taught by Gifford et al.

Thus, it would be advantageous to have a scanning system for scanning microarrays of biomolecules on microchips that is self-calibrating in that the sensitivity changes in the detection components are compensated for. Further, it would be advantageous to have a scanning system that could provide absolute target concentration measurement results where the results are reproducible from scanner to scanner. Still further, it would be advantageous if such self-calibration could be integrated into the scanner and the calibration be performed automatically.

SUMMARY OF THE INVENTION

The present invention provides a novel self-calibrating scanning system and method of calibrating which are useful for scanning microarrays of biomolecules on microchips. Since the present system is a scanning system that scans microarrays of minute quantities of biomolecules, a laser or other stable collimated light source is typically used as the excitation light source. The laser is characteristically very stable, such that the need to account for variations in excitation light on the system is essentially eliminated. The self-calibrating scanner and method compensate, and may also monitor, for changes in the component whose sensitivity will most likely to drift or vary with time and use, i.e., the detection components. Further, for scanning systems with multichannel detection components, the calibration portion of the invention can be made fairly redundant without much extra effort, if any. The self-calibrating scanner is particularly useful in scanning fluorometry of arrays. The self-calibrating scanner provides calibration capability of the specific sensitivities/scale factors in the detection color channels.

In one aspect of the invention, the self-calibrating scanning system comprises an excitation light source that produces an excitation light, an optics portion, a detection portion, and a calibration portion. The optics portion directs the excitation light from the excitation light source to a microarray of labeled biomolecules on a microchip that is under test. The detection portion comprises a detector that detects or measures emissions from labels on the microarray that are excited by the excitation light and produces an output signal responsive to the detected emissions. The calibration portion comprises a calibration apparatus and a compensation portion. The calibration apparatus comprises a calibration light source and optionally a calibration detector for ensuring a constant or calibrated light level from the calibration light source via a closed feedback control loop. The compensation portion comprises components to perform one or more of data collection, data storage, data comparison, data communication, and adjustment to the scanning system to compensate for any changes.

The calibration apparatus provides a calibrated light to the detection portion of the scanner. The detection portion measures the calibrated light and provides a corresponding output. The compensation portion measures or collects the output from the detection portion corresponding to the calibrated light and may compare the output to a stored reference value. If the output is different from the stored reference value, i.e., there is a change in detection sensitivity, the compensation portion compensates for the sensitivity change, either by adjusting the detection portion or providing sensitivity data for analysis. Such provided sensitivity data may be stored in a memory (for example, in association with data read from the array in response to excitation light). Any sensitivity data herein may be an indication of any change in sensitivity, so that such differences can be used in the processing of read data from an array to substantially compensate for the sensitivity changes, for example, which occurred between scanning different arrays. Alternatively, the sensitivity data may simply be an indication that sensitivity did not change, for example that between the scanning of arrays sensitivity remained constant, allowing a user to confidently compare results from arrays scanned at different times (or from different machines if any or no change in sensitivity with regard to a reference value is provided, or an absolute sensitivity value provided). The calibration portion can provide periodic calibration checks of the detection portion. The calibration portion may be a discrete unit or integral to the scanning system. The scanning system optionally further comprises an analysis portion. Alternatively, the scanning system may be otherwise associated with analysis equipment. The analysis portion comprises one or more of data collection, storage and analysis equipment components. The analysis portion receives the output signals from the detection portion and provides array data, such as the concentration of target in each location on the microarray. The analysis portion may further receive the sensitivity change data from the compensation portion, so that the sensitivity change data can be correlated with the array data.

The self-calibrating scanner of the invention compensates for sensitivity changes in the detection portion of the system to provide an absolute amount or concentration of target material on the microchip, not a relative amount, as in Gifford et al. (cited supra). Advantageously, the same microchip can be analyzed on other self-calibrating scanners of the present invention for the target concentration on the same microchip and the results will be substantially the same. In contrast, the system described by Gifford et al. essentially would not work for scanning minute quantities on arrays, and further, provides only relative target concentration values for bulk samples in a flow cell. Therefore, it is unlikely that any two or more systems described Gifford et al. will provide the same result for the same bulk sample/flow cell. The present invention does not determine target concentration on a relative scale. Advantageously, the present invention provides absolute results that are reproducible from one self-calibrating scanning system to another self-calibrating scanning system of the invention.

In another aspect of the invention, a method of calibrating a scanning system is provided. The method comprises the step of initially calibrating the detection portion of the scanner. The step of initially calibrating comprises the steps of generating a fixed signal (corresponding to the calibrated light level mentioned above) and measuring an output signal from the detection portion of the scanner in response to the fixed signal. The step of measuring may be repeated one or more times. The measurements are recorded and the mean value is calculated and stored as one reference value. The calibration apparatus and compensation portion described above may be used in the step of initially calibrating.

An additional aspect of the present invention may include simply retrieving from a memory stored sensitivity data and read data from an array, and correcting the read data based on the stored sensitivity data. Alternatively, another aspect may involve retrieving stored sensitivity data for respective different arrays (or different readings of the same array) and retrieving respective sensitivity data and, when the sensitivity data indicate no change in sensitivity, then comparing results from the different arrays (or different readings) or, when the sensitivity data indicates differences in sensitivity when the respective array readings were taken, then first correcting the read data from the different arrays (or different readings of the same array) then comparing the read results from them.

The method further comprises the step of subsequently calibrating the detection portion of the scanning system. The step of subsequently calibrating comprises the steps of separately generating another fixed signal that corresponds to the fixed signal mentioned above, using the calibration portion, as described above, measuring the corresponding output signal from the detection portion and comparing the corresponding output signal to the reference value, and compensating for any changes in sensitivity of the detection portion with respect to array data collected during a scan. The step of compensating comprises one or both of adjusting the detection portion of the scanning system to achieve a corresponding detection portion output signal with minimum deviation from the stored reference value, or providing detection sensitivity change data for analysis, so as to substantially compensate for any sensitivity changes for a scanned array. The step of subsequently calibrating may be repeated periodically and may be automatically or manually initiated. Moreover, implementation of the method of calibrating a scanning system in accordance with the invention can be automatic or manual. The present method helps to maintain throughput while reducing variations in detection sensitivity over time, such that the scanning system provides a substantially consistent accuracy level.

BRIEF DESCRIPTION OF THE DRAWINGS

The various features and advantages of the present invention may be more readily understood with reference to the following detailed description taken in conjunction with the accompanying drawings, where like reference numerals designate like structural elements, and in which.

MODES FOR CARRYING OUT THE INVENTION

Typical "biopolymer" array construction and different scanning methods and apparatus are described in detail in, for example, U.S. patent application Ser. No. 09/846,125, filed Apr. 30, 1991 and entitled "Reading Multi-Featured Arrays" by inventors Delenstarr et al., and the references cited therein which are incorporated herein by reference.

A "processor" in the present application references any combination of hardware or software which can control components as required to execute recited steps and includes, for example, a general purpose digital microprocessor suitably programmed (for example, from a computer readable medium carrying necessary program code or by communication from a remote location) to perform all of the steps required of it, or any hardware or software combination which will perform those or equivalent steps. A "memory" is any suitable device in which data can be stored and retrieved such as magnetic, optical, or solid state storage devices (including magnetic or optical disks or tape or RAM, or any other suitable device, either fixed or portable).

It is common practice to scan a microarray more than once during analysis, especially when fluorescent labels are used, and the light levels measured during the subsequent scans are typically compared. Therefore, in scanning hybridized samples, one skilled in the art wants to make sure that the sensitivity of the detection system components do not change unnoticed over time. If more than one fluorescent dye is used (e.g. in scanning gene expression chips using competitive hybridization) this becomes even more desirable. When changes in sensitivity in detection components occur unnoticed, the unknown difference in sensitivity changes for each different fluorescent dye results in apparent changes in the measured ratio of the different dye signals to be compared, thus possibly introducing systematic errors. As mentioned above, often the detector(s) used in fluorescent scanning are photomultiplier tubes (PMTs) that are known to age and to also deteriorate as a function of signals and overloads previously received.

Figure 1:
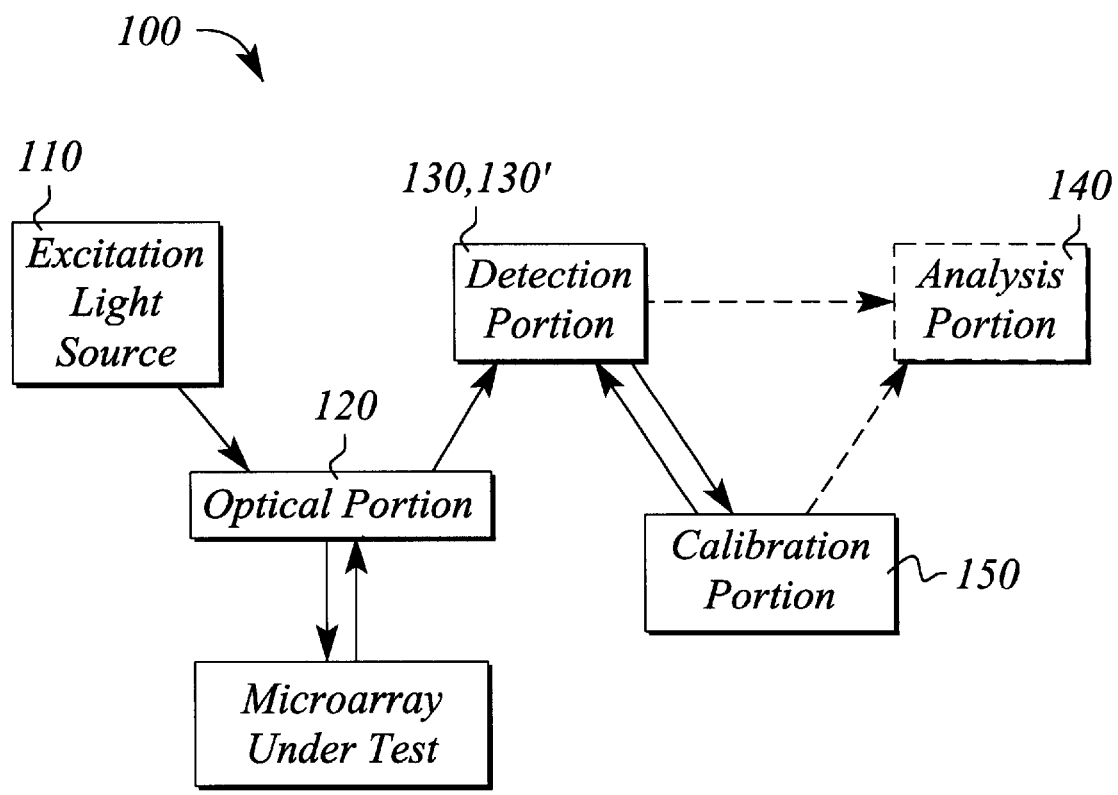
FIG. 1 illustrates a block diagram of a scanning system in accordance with the present invention.

A self-calibrating scanning system 100 for scanning arrays according to the invention is illustrated in FIG. 1. The scanning system 100 comprises a stable excitation light source 110, an optical portion 120 for directing collimated excitation light to a microarray of labeled biomolecule samples under test, a detection portion 130 for receiving light from the labeled test sample and converting the received light into a corresponding output signal, which can be analyzed to produce data about the array. The scanning system 100 optionally further comprises an analysis portion 140 for collecting and analyzing the output signal data from the detection portion 130. The optional analysis portion 140 is illustrated within a dashed-line box for that reason. The scanning system 100 further comprises a novel calibration portion 150, which interfaces with the detection portion 130 of the scanning system and optionally interfaces with the optional analysis portion 140. The present invention works particularly well with fluorescence scanners or scanning fluorometers.

The stable excitation light source 110 is either a laser or other collimated light source, which advantageously provides a substantially stable and consistent light intensity or power and controllable light beam during a scan. Further, the light intensity, power and beam are compatible with that necessary to excite the minute quantities of labels on the minute quantities of the biomolecules of the microarray without damaging them, while the collimated excitation light is scanned one or more times across the microchip array.

The optical portion 120 comprises an electro optic modulator (EOM) to modulate the light from the excitation light source and one or more mirrors, lenses and/or filters necessary to direct the collimated excitation light from the excitation light source 110 to the microarray sample. Further, the optical portion 120 can comprise one or more mirrors, lenses and/or filters necessary to direct the emissions from the excited labels on the microarray to the detection portion 130 of the scanning system.

The detection portion 130 comprises one or more detectors, such as a photomultiplier tube (PMT), to detect the emissions from the excited labels on the biomolecules. A PMT has the ability to detect the fluorescence emissions of interest in minute amounts or intensity levels. The detection portion 130 may comprise a multichannel detection scheme 130' (not illustrated), wherein each channel is designed to detect a different wavelength $\lambda$ range of the emission spectrum of interest and/or to provide redundancy to the detection capability of the detection portion 130. There is a PMT, or other detector, for each detection channel. The detector in each channel is adjusted to detect a particular emission range. Multichannel schemes 130' are particularly useful for separately detecting different labels (i.e., labels with different emission spectra), such as the well-known CY3 and CY5 fluorescence labels, which emit in the red/green color spectral ranges. While a PMT is suitable for detecting minute intensity levels for the invention, the PMT is notoriously subject to variations in its sensitivity due to at least environmental conditions (e.g., temperature) and age (e.g., time and usage). Without calibration, these sensitivity variations will affect the accuracy of the conventional scanning system in detecting the minute amounts of target material that were assayed with the biomolecules on the microarray. Therefore, the scanning system 100 with a self-calibrating capability of the invention is particularly advantageous for overcoming the conventional problems with scanning system accuracy.

The optional analysis portion 140 comprises one or more of data collection, storage, calculation and comparison capabilities, for example, to provide array data such as the absolute concentration or amount of a target sample in the microarray of biomolecules after a scan. The analysis portion 140 can provide the specific amount of a target at each feature location on the microarray. The analysis results provide valuable information about the target sample under test. The analysis portion 140 comprises a computer, such as a microprocessor, to perform the above capabilities. By 'optional' it is meant that the analysis portion 140 is not a necessary component for the operation of the scanning system 100 of the invention. The analysis portion 140 provides the additional capabilities described above to the inventive scanning system 100. Depending on the embodiment, the analysis portion 140 may be a separate component but provided by the system 100 provider or manufacturer, or may be a separate component and provided by a third party or the user of the system 100, and in both cases connected for communication to the scanning system 100, or the analysis portion 140 may be included, such as being integral to or interfaced with the basic inventive system 100 to provide the additional capabilities. Moreover, in one embodiment of the scanning system 100, one or more of the excitation light source 110, the optical portion 120, the detection portion 130 and the optional analysis portion 140 may be similar to that of a conventional scanning system. Any and all of these embodiments are within the scope of the invention.

Figure 3:
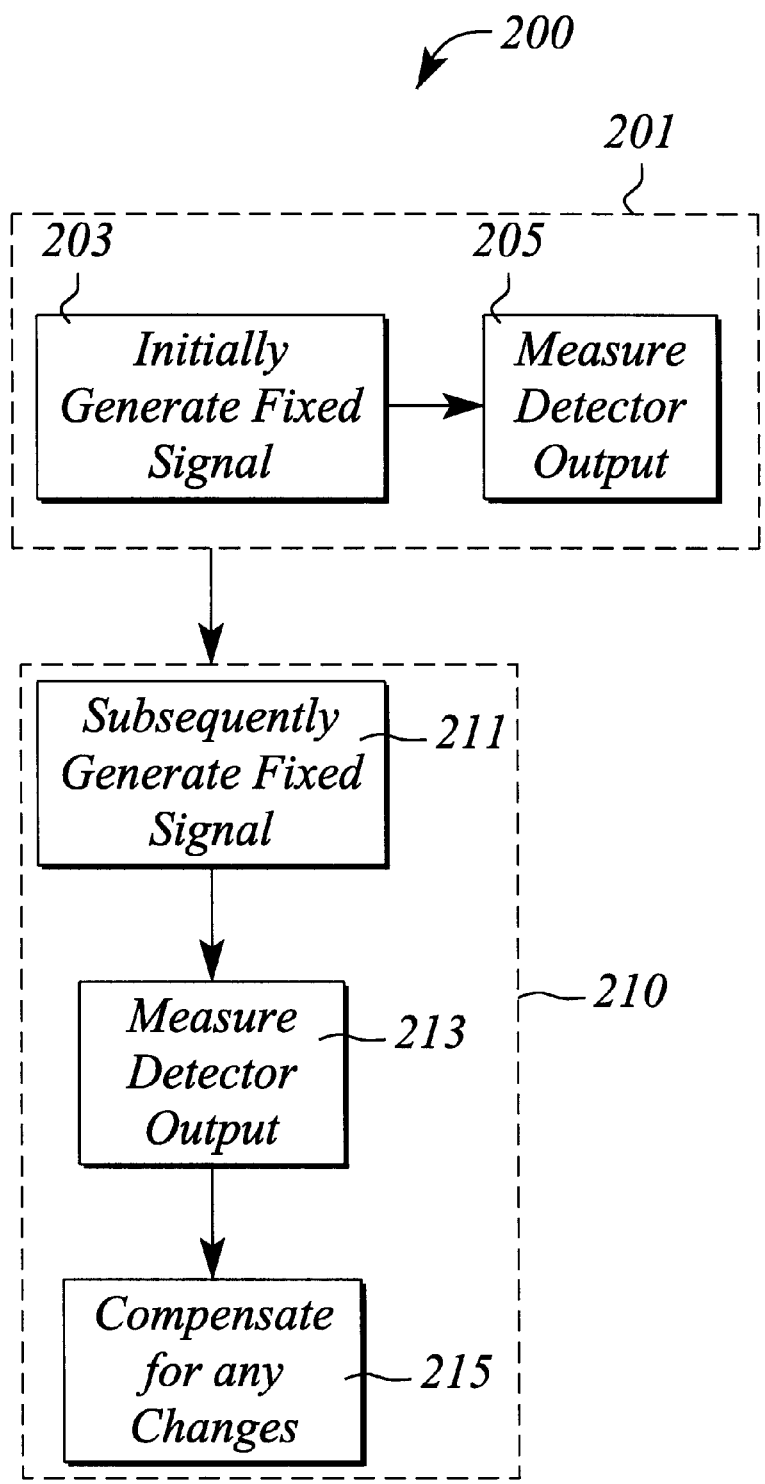
FIG. 3 illustrates a flow chart of a method of calibrating the scanning system of FIG. 1.

According to the invention, the scanning system 100 further comprises a calibration portion 150 comprising a calibration apparatus 160 and a compensation portion 180 further illustrated in FIG. 3. The calibration portion 150 essentially calibrates the detector portion 130. In one embodiment, the calibration portion 150 checks the sensitivity of the detection portion 130 for variations in its detector(s) and adjusts the PMT detector(s) to remove or compensate for the variation and maintain the accuracy of the scanning system 100. The calibration portion 150 adjusts the detection portion 130 to compensate for changes, so as to maintain the same dynamic range of detection for the scanning system 100. By "compensate" it is meant either at least in part maintaining the sensitivity to within a predetermined tolerance, which is preferably about zero. In other words, the calibration portion 150 ensures that a given signal of particular value emitted from the scanned array causes the same output signal to be generated from the detection portion 130 (within the predetermined tolerance) by, for example, changing amplifier gain or detector sensitivity (e.g. PMT voltage).

Alternatively, the calibration portion 150 can "compensate" for any changes in detection portion 130 sensitivity by making available the sensitivity data to correlate with array data after a scan. For example, the sensitivity data may be provided to the optional analysis portion 140, such that any sensitivity changes are taken into account during array analysis. For example, the sensitivity data from the calibration portion 150 can be stored for later access by, or added to, the array read data file. In this way, the analysis data is essentially compensated to account for the changes in the sensitivity of the detector portion 130.

Referring to FIG. 3, the calibration apparatus 160 comprises a calibration light source, and optionally may further comprise a calibration detector and a control to keep the calibration light source calibrated. The calibration light source may be any controllable light source, such as a lamp with filters (e.g., an incandescent lamp or an arc lamp, with e.g., an interference filter or a colored-glass filter), a LED or other solid-state emitter, for example, possibly with additional filters. By "controllable" light source, it is meant that the light source is highly reproducible (i.e., the light level is repeatable with little or no variation). The calibration light source emits a calibrated light at an output of the calibration apparatus 160. A signal associated with the calibrated light level may be detected by the optional calibration detector.

The calibration detector may be any stable detector, such as a photodiode or phototransistor, possibly with an integrated preamplifier, or a PIN diode, for example. By "stable" detector, it is meant that the detector is more stable in its sensitivity over time and temperature than a conventional PMT. The calibration detector measures the associated signal emitted by the calibration light source and produces an output signal corresponding to the measured associated signal that is received by the optional control, such as a control amplifier, for example.

The optional control comprises reference input value that corresponds to a preselected or reference light level and compares output signal received from the calibration detector to the reference input value. The reference light level should be big or high enough to be easily detected with good signal-to-noise ratio (SNR) and small or low enough to not saturate the detection signal path. By "good" SNR it is meant that the SNR is high enough to allow rapid measurement with an accuracy high enough to only contribute a minor fraction to the limit of the stability one is trying to achieve.

The reference light level is a light level (i.e., power or intensity) expected from the fluorescent tags or labels on the biomolecules of a microarray during a scan that will be detected by the detection portion 130 of a scanning system 100. There may be more than one reference light levels used to cover the spectral range of the tags that may be used with a microarray. Using the reference light levels as the calibrated light levels of the calibrated light from the calibrated light source ensures that the detection portion 130 is most sensitive in the desired spectral range of interest.

If necessary, the control adjusts the calibration light source to produce the calibrated light at the output of the calibration apparatus 160 at a fixed or constant level equal to the reference level (i.e., corresponding to the fixed signal mentioned below). The control electronically compares the output signal from the calibration detector to the reference input value and adjusts the current through the light source to increase or decrease its signal, as needed, for the two values to be the same. The calibration apparatus 160 produces a highly reproducible calibrated light that, in one embodiment, is provided in a closed loop control (i.e., such that the area over which the power is distributed is constant). The closed loop control may use a regulator or a servomechanism. The calibration apparatus 160 may be an off-the-shelf unit, for example an IPL 10630 Series Self Monitoring Emitter manufactured by Integrated Photomatrix, Ltd., England. The calibration apparatus 160 may be a stand-alone unit, or preferably is integrated into the scanning system 100.

The calibration apparatus 160 periodically provides the calibrated light at its output to the detection portion 130 of the scanning system 100, either manually or automatically. The detection portion 130 detects the calibrated light and generates an output signal in response to the calibrated light. The responsive output signal from the detection portion 130 can be monitored for changes in sensitivity to the calibrated light. The compensation portion 180 measures the output signals from the detection portion 130 that are responsive to the calibrated light.

The compensation portion 180 comprises one or more of signal data collection, calculation, storage and comparison and adjustment capabilities. In one embodiment, the compensation portion 180 has the ability to adjust the system 100, in particular the detection portion 130, using a digital to analog converter, for example. In another embodiment, the compensation portion 180 can be accomplished with the analysis portion 140 and the compensation portion 180 further comprises the digital to analog converter for the adjustment capability not found in a conventional analysis portion of a microarray scanner. In other embodiments, the compensation portion 180 provides the above-mentioned capabilities either redundantly to the analysis portion 140 or in part shared with the analysis portion 140. In these embodiments, the compensation portion 180 may further comprise one or more of memory, a processor or computer. The compensation portion 180 collects the output signal data from the detection portion 130 that is responsive to the calibrated light and stores the signal data. Further, the compensation portion 180 has stored therein a reference value or initial output signal provided upon initial calibration of the system 100, described further below, and/or provided during a previous calibration. The compensation portion 180 compares the reference or initial value to the responsive output signal for changes in sensitivity.

In one embodiment of the compensation portion 180, if a change is noted, the compensation portion 180 adjusts the detection portion 130 so that the output signal equals the reference value to compensate for the change. The compensation portion 180 may adjust the PMT voltage, for example, to adjust the system gain and compensate for the variation that was detected by the calibration portion 150. Advantageously, the compensation portion 180 can store the adjustments made during a calibration to simplify future settings, as described further below. In another embodiment, the compensation portion 180 stores measurements and notes measurement changes in the memory that is associated with file data gathered on the array being evaluated by the scanning system 100. In this embodiment, the compensation portion 180 would provide a message that indicated whether a change was noted or not and the magnitude of the change, so that the detected change can be compensated for in scanned array data.

The calibration portion 150 according to the invention, provides a closed loop control of the detection portion 130 of the scanning system 100. The calibration portion 150 provides for initial calibration of the system 100, preferably at the factory, and a subsequent calibration of the system, preferably in the field, one or both of which may be manual or automatic, as are further described below with respect to the method of the present invention. The calibration portion 150, or at least the calibration apparatus 160 thereof, is integrated into the scanning system 100 of the invention in the preferred embodiment. Further, advantageously a conventional scanning system may be adapted to use the calibration portion 150 with only minor modifications to the conventional system.

The calibration portion 150 may further comprise optics and/or filters. Optics may be employed to distribute the calibrated light from one calibrated light source of the calibration apparatus 160 to multiple detectors in the detection portion 130 of the scanning system 100. Further, optics, such as a light guide, a mirror, a scattering screen or a relay lens, for example, may be employed to make delivery of the calibrated light from the calibrated light source to the detectors more efficient. Filters may be used to suppress unwanted radiation, and/or to attenuate overly strong signals, and/or to have the spectrum from the calibrated light source more closely correspond to that of the tags or labels to be detected on the microarray under test.

The calibration portion 150 of the present invention is versatile and adaptable to different multichannel schemes 130' in the scanning system 100. For example, in one embodiment of the calibration portion 150, the controllable light source of the calibration apparatus 160 may comprise a single lamp that is used with more than one different filters, such that the calibration apparatus 160 could be used to provide more than one different levels of the calibrated light from the calibration portion 150 for calibration of multiple detectors of the detection portion 130 of a multichannel system 130'. Advantageously, a single calibration light source used to calibrate all detectors in the detection multichannels reduces cost. In another embodiment, the calibration portion 150 may comprise a calibration apparatus 160 with either a single calibration light source to calibrate the response of a single detector or multiple calibration light source(s) to calibrate the response of multiple detector(s) in the detection portion 130, 130' of the scanning system 100.

Alternatively, the calibration portion 150 may comprise more than one calibration apparatuses 160 for the same purpose. Further, where the calibration apparatus 160 comprises multiple calibration light sources, the multiple light sources may be used to calibrate the response of one detector in the detection portion 130 of the scanning system 100, where one detector is used in multiple spectral ranges. This is particularly advantageous when a single calibration light source in the calibration apparatus 160 is unable to calibrate the multiple spectral ranges. In the preferred embodiment, the calibration portion 150 comprises a calibration apparatus 160 comprising one light source per 'color' detection channel of the multichannel detection portion 130', where the detector in each respective color channel is calibrated using one color-corresponding (i.e., spectrum- or wavelength-corresponding) light source.

Where the detection portion 130 comprises one detector used for detecting different colors, e.g., in consecutive scans with the self-calibrating scanner 100, the calibration portion 150 may comprise one or more calibration apparatuses 160, each with one or several calibration light sources equal to the number of different colors to be detected, such that there is at least one calibration light source that corresponds to a particular color. In this embodiment of the calibration portion 150, one compensation portion 180 can be used monitor and adjust the detector portion 130 to compensate for spectrally differential sensitivity changes. However, where the cost of device complexity outweighs the cost of redundancy, more than one compensation portion 180 may be used and still be within the scope of the invention.

Further, in the embodiment where one or more calibration apparatuses 160, each having one or several calibration light sources of different colors, is used in the calibration portion 150, it is not only possible to use each of the calibration light sources to remeasure a respective 'corresponding' detector of the detector portion 130, 130', but it may also be possible to make measurements with one or more of the calibration light sources on one, a few, or each detector of the detection portion 130, 130', thus making the calibration redundant in one calibration step.

Preferably, the scanning system 100 is first calibrated at the factory to take into account, e.g., variations from unit to unit in alignment and transmission of the optics portion 120. When the scanning system 100 is manufactured, a desired system scale factor is determined for the detection portion 130. The system scale factor is defined as signal counts per photons detected at fixed excitation power. The calibration portion 150 only needs to track the changes of the component most likely to change the sensitivity (scale factor) later, which advantageously, is expected to be only the detector(s) in the present scanning system 100. The calibration portion 150 is used to make sure that the contribution of the detector(s) to the system scale factor remains constant (i.e., detector variations are minimized, but not necessarily zero).

A method 200 of calibrating the scanning system 100 includes both an initial calibration of the detection portion 130 when the scanning system 100 is first manufactured, and also subsequent calibration of the detection portion 130 when the scanning system 100 is in the field. The method 200 essentially compensates for detector sensitivity changes by measuring the output signal from the detection portion 130 responsive to an initial calibration, and in one embodiment, adjusting the system gain during a subsequent calibration, such that the output signal from the detection portion remains substantially the same. In another embodiment, instead of physically adjusting the system 100, the method 200 compensates by storing sensitivity change data for use with the scanned array file data, so that accurate information about target samples can be ascertained.

Figure 2:
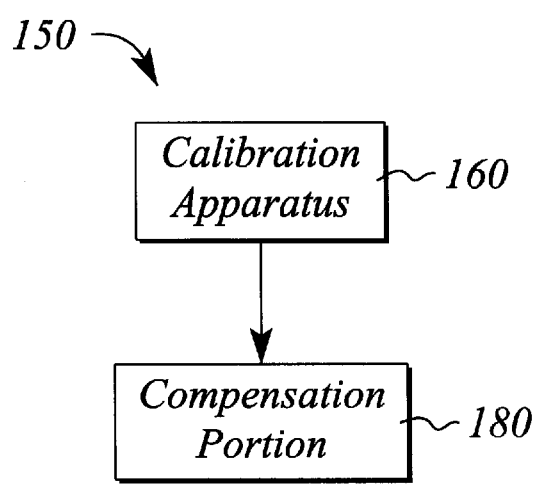
FIG. 2 illustrates a block diagram of the calibration portion of the scanning system of FIG. 1.

The method 200 of calibrating is illustrated in block diagram in FIG. 2. The method 200 comprises the step of initially calibrating 201 the detection portion 130 of the self-calibrating scanning system 100. After the system 100 is manufactured, but before its first use by a user, the initial calibration 201 is performed. In a preferred embodiment, the step of initially calibrating 201 is performed at the factory where the system 100 is manufactured. However, the initial calibration step 201 can be performed at the site of use (i.e., the user's facility). The step of initially calibrating 201 comprises the step of generating 203 a fixed signal (corresponding to the calibrated or preselected light level mentioned above) with the calibration apparatus 160 of the calibration portion 150 of the scanning system 100. Alternatively, the fixed signal may be provided by some other source that reproducible produces the same fixed signal. The step of initially calibrating 201 further comprises the step of measuring 205 an initial output signal from the detection portion 130 in response to the fixed signal with the compensation portion 180. Again alternatively, another measurement component other than the compensation portion 180 may be used to take the measurements. The measurements are made one or more times, and preferably are repeated as needed to obtain sufficient SNR. The measurements are recorded and the mean signal value (hereinafter 'initial output signal' or 'reference value') is calculated and stored in the compensation portion 180 of the scanning system 100.

It is this stored initial output signal value that is the standard or reference for the subsequent calibration of the scanning system 100 in the field. Preferably, every scanning system 100 of the invention that is initially calibrated 201 in accordance with the invention will perform substantially the same to the same fixed signal. Advantageously, a user can expect consistency between scanning systems 100 of the invention and reproducibility of the microarray scanning results.

The method 200 further comprises the step of subsequently calibrating 210 the detection portion 130 of the scanning system 100. The step of subsequently calibrating 210 comprises the steps of separately and subsequently generating 211 another fixed signal that corresponds to the first mentioned fixed signal from the calibration portion 150; measuring 213 the output signal from the detection portion 130 that is responsive to the subsequently generated 211 fixed signal; and compensating 215 for any change between the initial output signal and the subsequent output signal. In one embodiment, the step of compensating 215 comprises adjusting, if necessary, system gain to have a resulting output signal deviate as little as possible from the stored initial output signal. The system gain is adjusted by adjusting the detector(s) voltage in the detection portion 130, 130', or with a digital potentiometer, for example. In another embodiment, the step of compensating 215 comprises providing data corresponding to the sensitivity change for analysis. The step of providing comprises storing the sensitivity change data in a file in a memory that is made available to an array read data file that contains data collected on a scanned array. Further, the step of providing the sensitivity change data may comprise displaying whether a sensitivity change was detected during a calibration that can be correlated to particular array scans. The array data can be corrected, if necessary, to compensate for the sensitivity changes either manually or automatically, using the compensation portion 180 and/or the analysis portion 140.

The step of subsequently calibrating 210 is performed in the field and may be repeated 217 periodically. Preferably, the first subsequent calibration 210 is performed prior to a first scan of an actual microarray under test in the field. In one embodiment, the step of subsequently calibrating 210 can occur automatically at a predetermined time, such as the first scan mentioned above. The subsequent calibrations 210 may be repeated 217 manually or automatically at certain predefined or predetermined time intervals, such as once a day or once a week, for example. Other examples include repeating 217 the step of subsequently calibrating 210 prior to performing the first scan of each different microarray under test; and each time the power to the scanning system 100 is turned from OFF to ON, or more or less frequently. How often the subsequent calibration step 210 is repeated 217 may depend on a trade-off between system performance level and instrument throughput. Therefore, whether the step of subsequently calibrating 210 is repeated 217 and the frequency of the repetitions 217 are not intended to limit the scope of the invention. What is important is that the method 200 of the invention advantageously can repeat 217 the step of subsequently calibrating 210 in the field, either manually or automatically.

The method 200 of calibrating the scanning system 100 in accordance with the invention compensates for variations in the detector sensitivity over time, so that the measurements taken during a scan of a microarray under test are more accurate and reliable. Moreover, the method 200 is readily automated, for example with a computer or microprocessor in the compensation portion 180 or in the optional analysis portion 140, such that the scanning system 100 provides a substantially consistent accuracy level. Still further, the method 200 provides monitoring and actual calibration or adjustment capabilities, which advantageously provides the user with absolute measurements results of the microarray under test. The absolute measurement results are also advantageously reproducible from one scanning system 100 to another in accordance with the invention.

As mentioned above, the initial calibration step 201 may be performed at the same location as the subsequently calibration step 210 is performed, or preferably, may be performed at a first location remote from a second location where the subsequent calibration step 210 is performed. Further, the subsequent calibration step 210 may be initiated from a third location remote from the second location of the self-calibrating scanning system 100. Still further, the third location may be the same or remote from the first location where the initial calibration was performed. The results of the initial calibration may be included in the calibration portion 150 of the self-calibration scanning system 100 when shipped to the user, or otherwise be readily available at the time of the subsequent calibration step 210 at the second location. The initial calibration results, or information relating to the calibration results, can be forwarded (such as by communication) to the self-calibrating scanning system 100 at the second location. And the subsequent calibration results, or related information, can be forwarded to the first or third location or another remote location and be within the scope of the invention.

A location is "remote" if it is at least a different location, including but not limited to, a different room in a building, a different building, a different city, different state or different country, or if the location is at least one, at least ten, or at least one hundred miles apart, for example. "Communicating" information means transmitting the data representing that information as electrical signals over a suitable communication channel (for example, a private or public network). "Forwarding" information refers to any means of getting that information from one location to the next, whether by physically transporting that information or otherwise (where that is possible) and includes, at least in the case of data, physically transporting a medium carrying the data or communicating the data. Moreover, as used herein, the term "user" includes for example, a purchaser of the system 100, an operator of the system 100, or an agent of the user, purchaser, or operator, wherein an agent includes for example, a parent or subsidiary organization, an employee or officer of the user, purchaser or operator, or of any of their parent or subsidiary organizations, a customer, a subcontractor, vendor, an independent contractor of any of the aforementioned, or the like.

Thus, there have been described a novel self-calibrating scanning system 100 and method 200 of calibrating the scanning system 100. It should be understood that the above-described embodiments are merely illustrative of the some of the many specific embodiments that represent the principles of the present invention. Clearly, those skilled in the art can readily devise numerous other arrangements without departing from the scope of the present invention.

What is claimed is:

1. A self-calibrating scanning system for scanning a microarray of biomolecules comprising:
    an excitation light source that produces an excitation light;
    an optics portion that directs the excitation light from the excitation light source to the microarray of biomolecules;
    a detection portion that produces an output signal responsive to an emission detected from a label on the microarray being scanned with the excitation light; and
    a calibration portion that calibrates sensitivity of the detection portion, the calibration portion comprising:
        a calibration apparatus that produces a calibrated light at a reference light level that is detected by the detection portion; and
        a compensation portion that compensates for changes in the sensitivity of the detection portion, or which saves an indication of sensitivity in a memory in association with data read from the array in response to illumination with excitation light.

2. The self-calibrating scanning system of claim 1, wherein the calibration apparatus comprises a calibration light source that consistently reproduces the calibrated light.

3. The self-calibrating scanning system of claim 2, wherein the calibration apparatus further comprises a calibration detector and a control in a closed loop to provide reproducibility of the calibrated light from the calibration light source.

4. The system of claim 3, wherein the calibrated light source is selected from a lamp with a filter, a solid state emitter, or a light emitting diode, the calibration detector is selected from a photodiode or phototransistor, the control is a control amplifier, and the closed loop is provided by a regulator or servomechanism.

5. The self-calibrating scanning system of claim 1, wherein the compensation portion comprises a reference value corresponding to an initial output value from the detection portion responsive to the reference light level.

6. The self-calibrating scanning system of claim 5, wherein the compensation portion further comprises one or more of a computer, a processor and memory to optionally provide an indication and a magnitude of the change in sensitivity.

7. The self-calibrating scanning system of claim 6, wherein the compensation portion further comprises a digital to analog converter to adjust the detection portion when there is a change in sensitivity.

8. The self-calibrating scanning system of claim 6, wherein the reference value is stored in the memory, and wherein the change in sensitivity is indicated by a difference between the reference value and an output value from the detection portion responsive to the calibrated light.

9. The self-calibrating scanning system of claim 5, wherein the compensation portion further comprises a digital to analog converter to adjust the detection portion when an output value from the detection portion responsive to the calibrated light differs from the reference value.

10. The self-calibrating scanning system of claim 5, wherein the compensation portion indicates if an output value from the detection portion responsive to the calibrated light differs from the reference value and saves a magnitude of the difference for reference.

11. The self-calibrating scanning system of claim 1, further comprising an analysis portion that comprises one or more of a computer, a processor and memory to collect and analyze the output signal from the detection portion and to produce information about the labeled biomolecule.

12. The self-calibrating scanning system of claim 11, wherein the compensation portion uses a respective one or more of the computer, the processor and the memory of the analysis portion to provide an indication and a magnitude of the change in sensitivity for use with the information about the labeled biomolecule.

13. The self-calibrating scanning system of claim 1, wherein the excitation light source comprises one of a laser or other light source that produces the collimated light, and the detection portion comprises a photomultiplier tube detector, and the system further comprising an optional analysis portion that comprises a microprocessor.

14. The system of claim 1, wherein the calibration portion is integral to the scanning system.

15. The system of claim 1, wherein the calibration apparatus is integral to the scanning system.

16. The system of claim 1, wherein the calibration portion further comprises one or more of an optical component and a filter, wherein the optical component efficiently distributes the calibrated light to a detector in the detection portion, and the filter attenuates signal noise from reaching the detection portion.

17. The system of claim 1, wherein the calibration portion further comprises a filter to modify the calibrated light to correspond to the emission from the scanned label on the microarray.

18. The system of claim 1, wherein the detection portion comprises multiple channels having a photomultiplier tube in each channel, and wherein the calibration portion further comprises a filter, and wherein the calibration apparatus and the filter provide different calibrated light levels from the calibration portion to the multiple channels of the detection portion.

19. The system of claim 1, wherein the calibration apparatus comprises a plurality of calibration light sources, with different ones of the calibration light sources emitting a different calibrated light at a different reference light level that corresponds to an emission in a different spectral range from a scanned label on the microarray of biomolecules, and wherein the detection portion comprises a photomultiplier tube detector to detect the emissions in the different spectral ranges.

20. The system of claim 1, wherein the detection portion comprises a plurality of different color channels to detect emissions in a plurality of different color spectral ranges, each different color channel comprising a photomultiplier tube detector, and wherein the calibration portion comprises a plurality of calibration apparatuses, at least one different calibration apparatus for each different color channel, such that the photomultiplier tube detector in each color channel is calibrated with one corresponding color calibrated light.

21. In a scanning system for scanning a microarray of labeled biomolecules that has an excitation light source that produces a stable collimated light, an optics portion, and a detection portion, the improvement comprising:

a calibration portion for calibrating sensitivity of the detection portion, the calibration portion comprising:

a calibration apparatus that produces a calibrated light at a preselected light level that is detected by the detection portion; and a compensation portion that measures an output value from the detection portion responsive to the calibrated light, compares the output value to a reference value to determine whether the output value is different from the reference value, and compensates for any differences.

22. The system of claim 21, wherein the compensation portion compensates by adjusting the detection portion when a difference in values is determined so as to make the difference equal or to approach zero.

23. The system of claim 21, wherein the calibration portion monitors the sensitivity of the detection portion periodically.

24. The system of claim 21, wherein the compensation portion compensates by providing a magnitude of difference between the output value and the reference value to an array read file for analysis.

25. The system of claim 24, wherein the compensation portion further compensates by displaying whether a difference was determined.

26. The system of claim 21, wherein the calibration portion is integral with the scanning system.

27. The system of claim 21, wherein the calibration apparatus is integral with the scanning system.

28. The system of claim 21, wherein the calibration apparatus comprises:

a calibration light source that consistently reproduces the calibrated light; and optionally further comprises:

a calibration detector that measures a signal from the calibration light source corresponding to the calibrated light; and a control connected between the calibration light source and the calibration detector that can adjust the calibration light source in a closed loop when needed, such that the calibration light source consistently reproduces the calibrated light at the preselected light level.

29. The system of claim 21, further comprising an analysis portion, wherein all or part of the compensation portion is incorporated into the analysis portion.

* * * * *